United States Patent [19]

Mori et al.

[11] Patent Number: 4,511,726
[45] Date of Patent: Apr. 16, 1985

[54] PRODUCTION METHOD OF AN INSECT PHEROMONE

[75] Inventors: Kenji Mori, Tokyo; Tamon Uematsu, Funabashi, both of Japan

[73] Assignee: Sumitomo Chemical Company, Limited, Osaka, Japan

[21] Appl. No.: 449,748

[22] Filed: Dec. 14, 1982

[30] Foreign Application Priority Data

Dec. 24, 1981 [JP] Japan .............................. 56-214181
Dec. 28, 1981 [JP] Japan .............................. 56-211415
Feb. 17, 1982 [JP] Japan .............................. 57-25168
Mar. 17, 1982 [JP] Japan .............................. 57-43599
Mar. 23, 1982 [JP] Japan .............................. 57-46938
Mar. 23, 1982 [JP] Japan .............................. 57-46939

[51] Int. Cl.$^3$ ........................................... C07D 311/02
[52] U.S. Cl. .................................................. 549/283
[58] Field of Search ........................................ 549/283

[56] References Cited

U.S. PATENT DOCUMENTS 4,296,036 10/1981 Mori et al. ........................ 549/283

FOREIGN PATENT DOCUMENTS 864926 4/1961 United Kingdom ................ 549/283

OTHER PUBLICATIONS

Journal of Chemical Ecology, vol. 3, No. 5, pp. 549-561 (1977).
The Canadian Entomologist, vol. 112, pp. 107-109 (1980).
Tetrahedron, vol. 36, pp. 2197-2208 (1980).
Journal of the Organic Chemistry, vol. 45, pp. 2290-2297 (1980).

Primary Examiner—Ethel G. Love
Attorney, Agent, or Firm—Stevens, Davis, Miller & Mosher

[57] ABSTRACT

A process for producing 3,3,7-trimethyl-2,9-dioxatricyclo[3.3.1.0$^{4,7}$]nonane useful as an insect pheromone and having the formula,

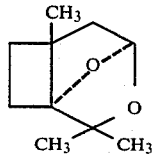

which comprises reducing 1,5,5-trimethyl-7-endo-tert-butyldimethylsilyloxy-4-oxabicyclo[4.2.0]octan-3-one with diisobutylaluminum hydride, and treating with an acid, after desilylation.

2 Claims, No Drawings

PRODUCTION METHOD OF AN INSECT PHEROMONE

The present invention relates to a method for producing 3,3,7-trimethyul-2,9-dioxatricyclo[3.3.1.0^{4,7}]-nonane (general name: lineatin) which is an aggregation pheromone of an ambrosia beetle and the optically active compounds thereof, and to the intermediates therefor and a method for producing the same.

Insect pheromones, because of their powerful attractant action on insects, have come to be recently used for controlling insect pests. It is however very difficult to isolate large quantities of pheromone from the natural world, so that the development of an economical synthetic method for pheromone is strongly demanded.

Lineatin is an aggregation pheromone isolated from the frass of female beetles of *Trypodendron lineatum*, and it is known to show an attractant action on the beetles and expected to be usable as an insect pests controlling agent [Journal of the Chemical Ecology, Vol. 3, 549 (1977)]. After that, it was reported by Borden et al. that the attractant action of lineatin arises from the (+)-isomer and that the (−)-isomer hardly shows such action [The Canadian Entomologist, Vol. 112, 107 (1980)]. Further, lineatin was synthesized and its chemical structure was determined by Mori et al. [Tetrahedron, Vol. 36, 2197 (1980)] and Slessor et al. [Journal of the Organic chemistry, Vol. 45, 2290 (1980)].

The present inventors found how to produce lineatin from dichloroketene and isoprene, the both being cheap raw materials, through following route:

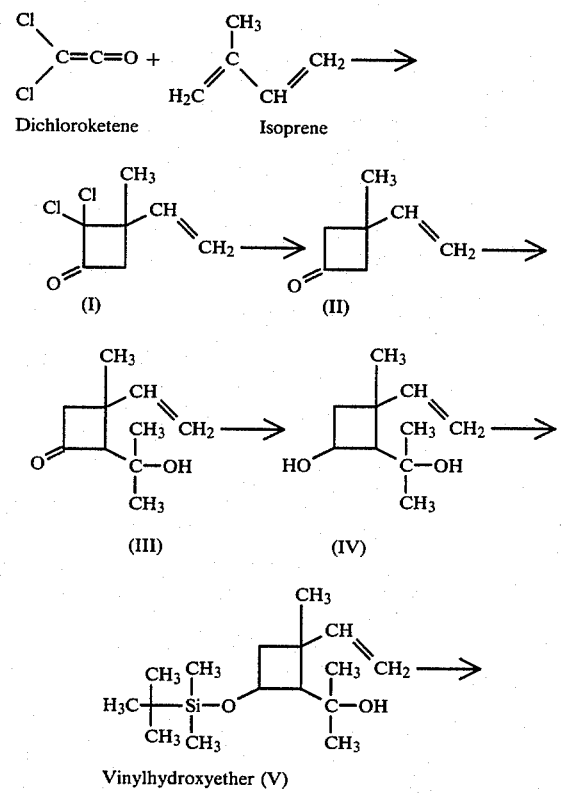

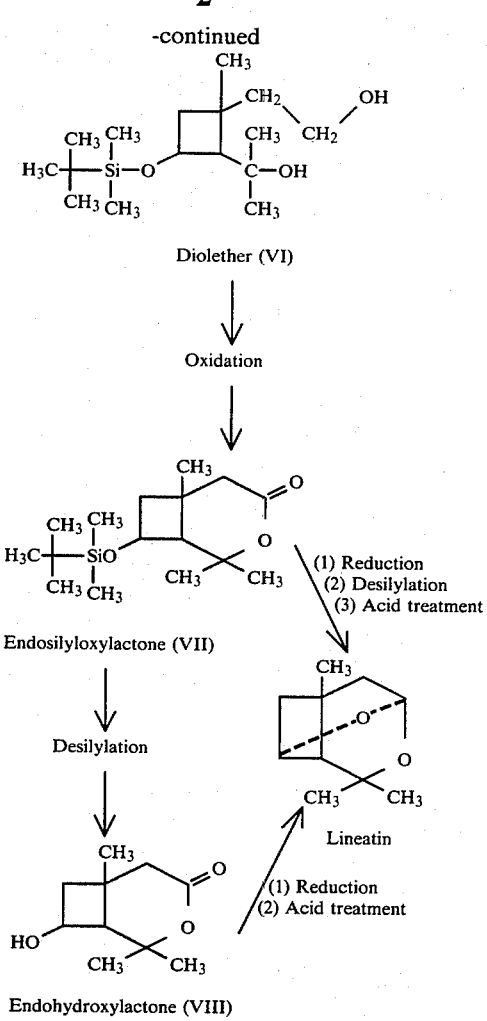

The route shown above will be explained. The compound (I) is first produced by the addition of dichloroketene to isoprene, and then it is converted to the compound (II) by reductive dechlorination. The compound (II) is condensed with acetone using lithium diisopropylamide to obtain the compound (III) which is then reduced into the compound (IV) with lithium tri-sec-butylborohydride. The secondary alcohol group of the compound (IV) is protected by the reaction with tertbutyldimethylsilyl chloride in dimethylformamide in the presence of imidazole to obtain the vinylhydroxyether (V) which is then converted into the diolether (VI) by hydroboration. The diolether (VI) is oxidized into the endosilyloxylactone (VII). The endosilyloxylactone (VII) is desilylated into the endohydroxylactone (VIII) which is then reduced and treated with an acid into lineatin.

Lineatin is also produced by reducing the endosilyloxylactone (VII), one of the intermediates of the route shown above, with diisobutylaluminum hydride, and treating with an acid after desilylation.

Hereupon isoprene which is one of the starting materials is a commercial product, and dichloroketene, another starting material, is a well-known compound (Tetrahedron, Vol. 27, 615–638, 1971).

Next, the present invention will be illustrated in detail.

(1) Production of 3-methyl-3-vinylcyclobutanone [Compound (II)]

The compound (II) can be produced by reducing 2,2-dichloro-3-methyl-3-vinylcyclobutanone [Compound (I); refer to Example 1] with zinc at a temperature between room temperature and the boiling point of a solvent for 3 to 30 hours in the presence of preferably not less than two equivalents of an acid.

As the solvent, lower alcohols such as ethanol, water and lower fatty acids such as acetic acid may be used alone or in mixtures of them or with other inert solvents. As the acid, hydrochloric acid, acetic acid, etc. are used. After completion of the reaction, after-treatment is carried out as usual, followed by purification by chromatography or distillation if necessary.

(2) Production of 1,5,5-trimethyl-7-endo-tert-butyldimethylsilyloxy-4-oxabicyclo[4.2.0]octan-3-one [Endosilyloxylactone (VII)]

The endosilyloxylactone (VII) can be produced by oxidizing 2-dimethylhydroxymethyl-3-methyl-3-(2-hydroxyethyl)-1-tert-butyldimethylsilyloxycyclobutane [Diolether (VI); refer to Examples 3 to 6] with not less than one equivalent of an oxidizing agent under reaction condition suitable for the oxidizing agent, in which case the hydroxyethyl group of the diolether (VI) is oxidized. When the reaction condition is not alkaline, the intended endosilyloxylactone (VII) having a formed ring is obtained. When the condition is alkaline, however, the endosilyloxylactone (VII) is obtained by acidification after the oxidation.

As the oxidizing agent, various ones may be used: Chromic acid type agents such as chromic acid, chromic acid anhydride and their modified ones (e.g. John's reagent, Cornforth reagent, pyridinium chlorochromate) (Fieser et al.: Reagents in Organic Synthesis, Vol. 1, 142–147, 1967); and dichromic acid type agents such as pyridinium dichromate, etc. Further, potassium permanganate, silver carbonate/celite and the like may also be used. The reaction is preferably carried out in the vicinity of neutrality, and pyridinium dichromate is particularly a preferred oxidizing agent. When pyridinium dichromate is used, commonly used solvents which are inert to oxidizing agents, for example, chlorinated hydrocarbons (e.g. methylene chloride, dichloroethane), ketones (e.g. acetone), ethers (e.g. diethyl ether, tetrahydrofuran) and the like may be used. In this case, the reaction temperature is 0° to 50° C., preferably 20° to 30° C., and the reaction time is 5 to 50 hours. After completion of the reaction, after-treatment is carried out as usual, followed by purification by chromatography or recrystallization if necessary.

(3) Production of 1,5,5-trimethyl-7-endo-hydroxy-4-oxa-bicyclo[4.2.0]octan-3-one [Endohydroxylactone (VIII)]

The endohydroxylactone (VIII) can be produced by desilylating 1,5,5-trimethyl-7-endo-tert-butyl-dimethyl-silyloxy-4-oxabicyclo[4.2.0]octan-3-one [Endosilyloxylactone (VII)] usually at about 0° C. to 50° C. for 1 to 10 hours in an inert organic solvent in the presence of not less than the equimolar amount of an acid or base. The inert organic solvent includes for example ethers (e.g. diethyl ether, tetrahydrofuran), hydrocarbons carbons (e.g. n-hexane, toluene), halogenated hydrocarbons (e.g. chloroform) and the like. As the acid, protonic acids such as acetic acid, hydrofluoric acid, etc. and Lewis acids such as boron trifluoride, iron chloride, etc. are used. As the base, special bases such as tetraalkylammonium fluoride, particularly tetra-n-butylammonium fluoride are preferred. After completion of the reaction, aftertreatment is carried out as usual, followed by purification by chromatography or recrystallization if necessary.

1,5,5-Trimethyl-7-exo-hydroxy-4-oxabicyclo-4.2.0]octan-3-one having the same planar structure as that of the endohydroxylactone (VIII) was synthesized by Mori et al. [Tetrahedron, Vol. 36, 2197 (1980)]. But this compound is different from the endohydroxylactone (VIII) in that the hydroxyl group at the 7-position takes an exoconfiguration.

(4) Production (a) of lineatin

Lineatin can be produced by reducing 1,5,5-trimethyl-7-endo-hydroxy-4-oxabicyclo[4.2.0]octan-3-one (Endohydroxylactone (VIII)] with diisobutylaluminum hydride of 2 to 3 times by mole based thereon at a temperature from −78° C. to room temperature (20° C.) for 10 minutes to 1 hour in an inert solvent; after acidification, acid-treating at a temperature from −78° C. to the boiling point of the solvent for 10 minutes to 5 hours; and extracting with a low-boiling solvent such as n-pentane, followed by drying and distillation.

The inert solvent includes for example ethers (e.g. diethyl ether), aromatic hydrocarbons (e.g. toluene), hydrocarbons (e.g. n-hexane) and the like. The acid includes for example protonic acids such as hydrochloric acid. Lineatin thus obtained is purified by column chromatography or distillation if necessary.

(5) Production (b) of lineatin

Lineatin can also be produced by reducing 1,5,5-trimethyl-7-endo-tert-butyldimethylsilyloxy-4-oxabicyclo[4.2.0]octan-3-one [Endosilyloxylactone (VII)] with diisobutylaluminum hydride of 1 to 1.5 time by mole based thereon at −78° C. to room temperature (20° C.) for 10 minutes to 1 hour in an inert solvent, adding an acid or base to the reaction solution and desilylating usually at 0° to 50° C. for 1 to 10 hours.

In this desilylation, the use of an acid causes ring closure to directly obtain the intended lineatin. When a base is used, by acidifying the reaction mixture by the addition of an acid such as hydrochloric acid or hydrofluoric acid and keeping the reaction solution in the vicinity of room temperature for several hours, ring closure is easily achieved to obtain the intended lineatin.

The inert solvent includes for example ethers (e.g. diethyl ether, tetrahydrofuran), aromatic hydrocarbons (e. g. toluene), hydrocarbons (e.g. n-hexane) and the like. As the acid, protonic acids (e.g. hydrochloric acid, hydrofluoric acid) and Lewis acids (e.g. boron trifluoride, iron chloride) are used. As the base, special bases such as tetraalkylammonium fluoride, particularly tetra-n-butylammonium fluoride are preferred. After completion of the reaction, aftertreatment is carried out as usual, followed by purification by distillation or column chromatography if necessary.

(+)-Lineatin, one of the optically active forms of lineatin, can be produced from racemic endohydroxylactone (VIII), which is an important intermediate for the aforementioned route, through the following route:

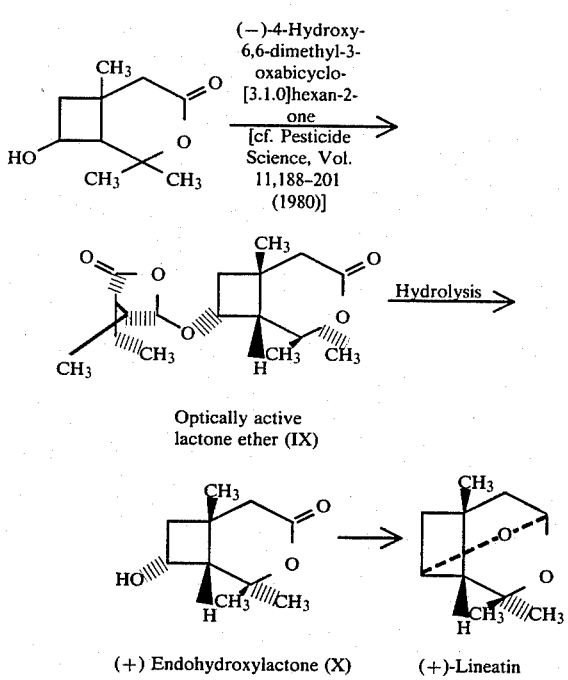

The (+)-endohydroxylactone can easily be produced by the hydrolysis or alcoholysis of an optically active lactone ether (IX) (refer to Example 11) which can be produced by reacting the (±)-endohydroxylactone and (−)-4-hydroxy-6,6-dimethyl-3-oxabicyclo[3.1.0]hexan-2-one, and separating the disastereomers. This hydrolysis is preferably carried out under an acidic condition. As the acid, there may be used 0.01 to 1 mole of various acids such as inorganic acids (e.g. hydrochloric acid, sulfuric acid) and organic acids (e.g. p-toluenesulfonic acid, methanesulfonic acid, formic acid). As the usable solvent, only water may be used, but alcohols (e.g. methanol, ethanol), ethers (e.g. diethyl ether, dioxane, tetrahydrofuran) and ketones (e.g. acetone), or mixtures with other common organic solvents are preferably used. The reaction proceeds thoroughly at room temperature, but heating may be applied depending upon the solvent. The reaction time is generally 0.5 to 5 hours.

Hereupon, (−)-4-hydroxy-6,6-dimethyl-3-oxabicyclo[3.1.0]hexan-2-one can easily be synthesized from (+)-cis-chrysanthemic acid (U.S. Pat. No. 1,270,270).

Next, the present invention will be illustrated specifically with reference to the following Examples.

EXAMPLE 1

Production of 2,2-dichloro-3-methyl-3-vinylcyclobutanone [Compound (I)]

A four-necked flask was dried by heating while passing nitrogen gas through it. After cooling, 68.1 g (1.0 mole) of isoprene, 74.2 g (1.1 mole) of activated zinc and 1.5 liter of ether were added, and while stirring, a mixture of 208.8 g (1.1 mole) of trichloroacetyl chloride and 159.5 g (1.04 mole) of phosphorus oxychloride was added dropwise at 10° to 25° C. over 2.5 hours.

After completion of the dropwise addition, the reaction mixture was stirred at 20° C. for 1 hour and then refluxed for 1 hour. After cooling, the reaction mixture was filtered through celite, and the filtrate was poured into 300 ml of ice water, washed with water, three 500-ml portions of a saturated aqueous sodium hydrogencarbonate solution and then with 500 ml of a saturated aqueous sodium chloride solution. The ehter layer was dried over anhydrous magnesium sulfate. After filtration, the filtrate was concentrated to obtain 154.8 g of an oily product (yield 86.5%). IR (neat, cm$^{-1}$): 1815, 1640, 990, 765

It was found by gas chromatographic analysis that the product was a mixture of 72% of the compound (I) and 22% of 2,2-dichloro-3-isopropenylcyclobutanone.

EXAMPLE 2

Production of 3-methyl-3-vinylcyclobutanone [Compound (II)]

To a four-necked flask were added 1 liter of acetic acid and 282.6 g (4.32 moles) of zinc powder, and while stirring, 154.8 g (0.81 mole, mixture) of the above crude mixture containing the compound (I) was added dropwise at 20° to 25° C. After stirring at room temperature for 24 hours and then at 70° C. for further 2 hours, the reaction mixture was cooled and 1 liter of ether was added thereto. The reaction mixture was filtered through celite, and 500 ml of water was added to the filtrate which was then neutralized with addition of sodium carbonate with stirring. The ether layer was washed with 500 ml of a saturated aqueous sodium chloride solution and dried over anhydrous magnesium sulfate. After filtration, ether was removed by evaporation from the filtrate which was then distilled to obtain 68.9 g of a liquid. This liquid was fractionally distilled to obtain 44.1 g of the intended compound (II) (yield 38.9%). Boiling point: 84°–85° C. (114 mmHg) $n_D^{24}$ 1.4408.

| Elementary analysis: | C (%) | H (%) |
| --- | --- | --- |
| Found | 75.99 | 9.09 |
| Calculated | 76.32 | 9.15 |

EXAMPLE 3

Production of 2-dimethylhydroxymethyl-3-methyl-3-vinylcyclobutanone [Compound (III)]

To a solution of 0.97 g (0.0096 mole) of diisopropylamine in 5 ml of tetrahydrofuran was added dropwise 6.9 ml (1.43 mole solution, 0.0099 mole) of n-butyllithium at −78° C. under argon atmosphere. Thereafter, 1.0 g (0.0091 mole) of the above compound (II) was added dropwise at the same temperature, and after stirring for 1 hour, 1.4 ml (0.0182 mole) of acetone was added dropwise at not more than −60° C., followed by standing overnight at −78° C. The reaction solution was poured into a cooled, saturated aqueous ammonium chloride solution and extracted with three 60-ml portions of ether. The ether layer was washed with a saturated aqueous sodium chloride solution and dried over anhydrous sodium sulfate. Ether was then removed by evaporation to obtain 1.24 g of the intended crude oily product. The result of gas chromatographic analysis showed that the product was a mixture of 36% of the cis-form and of the trans-form. This crude oily product was used as such for the subsequent reaction. IR (neat, cm$^{-1}$): 3460, 1775

EXAMPLE 4

Production of
2-dimethylhydroxymethyl-3-methyl-3-vinylcyclobutanol [Compound (IV)]

A solutaon of 1.24 g of the above compound (III) (purity 77%; 0.0057 mole) in 10 ml of tetrahydrofuran was added dropwise to 14.8 ml of lithium tri-sec-butylborohydride (a tetrahydrofuran solution of 1 mole concentration; 0.015 mole) at $-60°$ C. to $-70°$ C. under argon atmosphere. After stirring at $-74°$ C. for 1 hour, the temperature of the reaction solution was gradually raised. After 2 hours, an aqueous sodium acetate solution was added while ice-cooling, and then 4.7 ml of 30% aqueous hydrogen peroxide was added dropwise at 20° to 30° C. Tetrahydrofuran was removed by evaporation, the residual liquor was extracted with three 60-ml portions of ether, and the ether layer was washed with a saturated aqueous sodium chloride solution and dried over anhydrous sodium sulfate. After filtration, ether was removed by evaporation to obtain 1.76 g of the intended crude oily product.

IR (neat, cm$^{-1}$): 3360, 1635

EXAMPLE 5

Production of
2-dimethylhydroxymethyl-3-methyl-3-vinyl-1-tert-butyldimethylsilyloxycyclobutane [Compound (V)]

A solution of 1.76 g of the above compound (IV) and 1.51 g (0.022 mole) of imidazole in 4.5 ml of dimethylformamide was added to a solution of 1.11 g (0.0074 mole) of tert-butyldimethylsilyl chloride in 15 ml of dimethylformamide at room temperature, followed by stirring for 24 hours. The reaction mixture was poured into ice water and extracted with three 60-ml portions of ether. The ether layer was washed with water and then with a saturated aqueous sodium chloride solution, and dried over anhydrous sodium sulfate. After filtration, ether was removed by evaporation to obtain 2.19 g of a crude oily product. The product was then purified by silica gel column chromatography using a benzene/methylene dichloride mixed solvent as a developing solvent to obtain 0.66 g of the intended product.

IR (neat, cm$^{-1}$): 3540, 1638

EXAMPLE 6

Production of
2-dimethylhydroxymethyl-3-methyl-3-(2-hydroxyethyl)-1-tert-butyldimethylsilyloxycyclobutane [Diolether (VI)]

To 0.66 g (0.0024 mole) of the above vinyl-hydroxyether (V) was added dropwise 3.6 ml (0.0036 mole) of a tetrahydrofuran solution (1 M concentration) of borane at room temperature under argon atmosphere, followed by stirring for 14 hours. Thereafter, 3.5 ml of a tetrahydrofuran : water (2:1) mixed solution was added at 0° C., followed by stirring for 1 hour. Further, 3 ml of 3N aqueous sodium hydroxide solution and then 3 ml of a 30% aqueous hydrogen peroxide were added dropwise, followed by stirring at room temperature for 3 hours. Tetrahydrofuran was then removed by evaporation, and the residual liquor was extracted with three 60-ml portions of ether. The ether layer was dried over anhydrous magnesium sulfate, and after filtration, ether was removed by evaporation to obtain 0.9 g of crude oily product. This product was purified by column chromatography with silica gel and chloroform as a developing solvent to obtain 0.44 g of the oily intended product.

IR(neat, cm$^{-1}$): 3450

EXAMPLE 7

Production of
1,5,5-trimethyl-7-endo-tert-butyl-dimethylsilyloxy-4-oxabicyclo[4.2.0]octan-3-one [Endosilyloxylactone (VII)]

To 3.6 ml of methylene dichloride was added 1.44 g (0.00383 mole) of pyridinium dichromate, and to the resulting mixture was added dropwise 0.44 g (0.00146 mole) of the above diolether (VI), followed by stirring at room temperature for 36 hours. Thereafter, 50 ml of ether was added to the reaction mixture which was then filtered through celite. The filtrate was concentrated, 50 ml of n-hexane was added, and the mixture was filtered again through celite. The filtrate was concentrated to obtain 0.35 g of a crude oily product. This product was purified by multiple development on a silica gel thin layer chromatoplate using a hexane : acetone (5 : 1) mixed solvent to obtain 0.183 g of the intended endosilyloxylactone (VII) (yield 53%). m.p. 54°–56° C. This crystal was recrystallized from petroleum ether to obtain a crystal having a melting point of 60.5° to 61° C.

| Elementary analysis: | C (%) | H (%) |
|---|---|---|
| Found | 64.34 | 9.93 |
| Calculated | 64.37 | 10.15 |

EXAMPLE 8

Production of
1,5,5-trimethyl-7-endo-hydroxy-4-oxabicyclo[4.2.0]octan-3-one [Endohydroxylactone (VIII)]

To a solution of 0.109 g (0.366 mmole) of the endosilyloxylactone (VII) in 0.5 ml of tetrahydrofuran was added dropwise a solution of 0.37 ml (0.366 mmole) of tetra-n-butylammcnium fluoride in 0.2 ml of tetrahydrofuran at 0° C. under argon atmosphere, followed by stirring for 3 hours. Thereafter, 5 ml of a saturated aqueous ammonium chloride solution was added at 0° C., and tetrahydrofuran was removed by evaporation. The residual liquor was extracted with two 50-ml portions of ether, and the ether layer was washed with a saturated aqueous sodium chloride solution and dried over anhydrous sodium sulfate. After filtration, ether was removed by evaporation, and the crude oily product obtained was purified by thin layer chromatography in the same manner as above to obtain 45.6 mg of the intended oily endohydroxylactone (VIII) (yield 67.7%). This product was recrystallized from ether to obtain a crystal having a melting point of 64° to 65° C.

| Elementary analysis: | C (%) | H (%) |
|---|---|---|
| Found | 65.09 | 8.75 |
| Calculated | 65.18 | 8.77 |

EXAMPLE 9

Production (a) of 3,3,7-trimethyl-2,9-dioxatricyclo[3.3.1.0^{4,7}]nonane (lineatin)

To a solution of 39.7 mg (0.216 mmole) of the endohydroxylactone (VIII) in 0.3 ml of ether was added dropwise 0.27 ml of diisobutylaluminum hydride (25% hexane solution) while stirring at −74° C. under argon atmosphere. The temperature of the mixture was raised from −74° C. to −50° C. in 1 hour, and 0.63 ml of 1N hydrochloric acid was added at −50° C. The temperature was further raised to room temperature in 1 hour, and 0.08 ml of 6N hydrochloric acid was added, followed by stirring for further 1 hour. The reaction solution was extracted with three 10-ml portions of n-pentane, and the pentane layer was dried over anhydrous magnesium sulfate and filtered. n-Pentane was removed by evaporation to obtain 9 mg of a crude oily product (yield 25%). It was confirmed by gas chromatography/mass spectrometry that this oily product was identical with lineatin synthesized by Mori et al. according to the method described in the foregoing literature.

EXAMPLE 10

Production (b) of lineatin

To a solution of 69 mg (0.23 mmole) of the endosilyloxylactone (VII) in 0.5 ml of ether was added dropwise 0.17 ml of diisobutylaluminum hydride (25% hexane solution) while stirring at −74° C. under argon atmosphere. The temperature of the mixture was raised to −50° C. in 1 hour, and after adding one drop of water, 0.7 ml of 10% hydrofluoric acid was added, followed by stirring at room temperature for further 3 hours. The reaction solution was extracted with three 10-ml portions of n-pentane, and the pentane layer was dried over anhydrous magnesium sulfate and filtered. Thereafter, n-pentane was removed by evaporation to obtain a crude oily product. This product was purified by column chromatography with alumina and n-pentane as a developing solvent to obtain 7 mg of an oily product, lineatin (yield 18%).

EXAMPLE 11

Production of optically active lactone ether (IX)

1.5 Grams (8.14 mmole) of the (±)-endohydroxylactone (VIII), 1.16 g (8.14 mmole) of (−)-4-hydroxy-6,6-dimethyl-3-oxabicyclo[3.1.0]hexan-2-one [[$\alpha$]$_D^{23}$−97.3°-(c=1.0 ethanol), m.p. 113°–114° C.] and 12 mg of p-toluenesulfonic acid were dissolved in 50 ml of benzene, followed by refluxing by heating.

The formed water was removed azeotropically over 30 minutes, and then the solvent was removed by evaporation to obtain 2.82 g of a crude oily product.

This oily product was separated by column chromatography on silica gel (dichloromethane : acetone =50:1) and recrystallized from ethanol to obtain two diastereomers represented by the following formulae:

First eluted diastereomer (A):

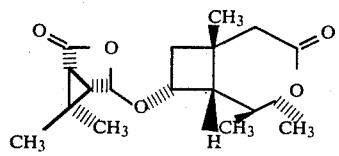

Yield 1.1 g (88%)
m.p. 143°–144° C.
[$\alpha$]$_D^{23}$−108.0° (c=1.06, ethanol)

| Elementary analysis: | C (%) | H (%) |
|---|---|---|
| Found | 66.24 | 7.87 |
| Calculated | 66.20 | 7.86 |

Later eluted diastereomer (B):

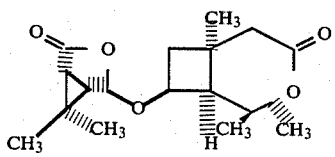

Yield 1.1 g (88%)
m.p. 124°–125° C.
[$\alpha$]$_D^{23}$−65.1° (c=1.02, ethanol)

| Elementary analysis: | C (%) | H (%) |
|---|---|---|
| Found | 66.31 | 7.96 |
| Calculated | 66.20 | 7.86 |

The absolute configuration of the diastereomer (A) obtained here was determined by X-ray crystal diffraction method. The diastereomer (A) was finally converted to (+)-lineatin. On comparing the diastereomers (A) and (B), (A) is more sparingly soluble in hydrocarbon solvents such as n-hexane than (B), which suggests a possibility that the both diastereomers may be separated from each other by recrystallization.

EXAMPLE 12

Production of the (+)-endohydroxylactone (X)

4.27 Grams (13.8 mmole) of the above diastereomer (A) was dissolved in 15 ml of methanol, and one drop of conc. hydrochloric acid was added at room temperature, followed by stirring for 2 hours. After adding 1 ml of a saturated aqueous sodium hydrogencarbonate solution, methanol was removed by evaporation, and the residue was dissolved in chloroform and dried over anhydrous magnesium sulfate. After filtration, chloroform was removed by evaporation to obtain a crude oily product. This product was purified by column chromatography on silica gel (chloroform : acetone=33 : 1), and then recrystallized from ether to obtain 2.2 g of the intended (+)-endohydroxylactone (X) (yield 86%). m.p. 90°–91° C.
[$\alpha$]$_D^{21.2}$+48.2° (c=1.0, carbon tetrachloride)

| Elementary analysis: | C (%) | H (%) |
|---|---|---|
| Found | 65.08 | 8.77 |
| Calculated | 65.18 | 8.77 |

EXAMPLE 13

Production of (+)-lineatin 1.7 Grams (9.23 mmole) of the above (+)-endohydroxylactone (X) was dissolved in 13.4 ml of dry ether, and after cooling to −74° C., 11.9 ml of diisobutylaluminum hydride (25% hexane solution) was slowly added dropwise to the resulting solution under argon atmosphere.

The temperature of the reaction solution was raised to −50° C. in 1 hour, and after adding 27.8 ml of 1N hydrochloric acid, the temperature was raised to room temperature over further 1 hour. Thereafter, 3.4 ml of 6N hydrochloric acid was added, followed by stirring for 1 hour. The reaction mixture was extracted with four 30-ml portoins of n-pentane, and the extracts were combined, washed with a saturated aqueous sodium chloride solution and dried over anhydrous magnesium sulfate. The solvent was then removed by evaporation to obtain 2.0 g of an oily product. This product was distilled to obtain 874 mg of the intended (+)-lineatin (Yield 56.3%). Boiling point: 110° C./53 mmHg $n_D{}^{21.7}$ 1.4586

$[\alpha]_D{}^{21.5}+85.8°$ (c=1.07, chloroform)

$[\alpha]_D{}^{21.5}+85.8°$ (c=1.03, n-pentane)

The NMR and IR spectra of this compound was completely identical with those of (±)-lineatin previously synthesized [Mori et al.: Tetrahedron, Vol. 36, 2197–2208, 1979].

What is claimed is:

1. 1,5,5-Trimethyul-7-endo-hydroxy-4-oxabicyclo-[4.2.0]octan-3-one.

2. (+)-1,5,5-Trimethyl-7-endo-hydroxy-4-oxabicyclo-[4.2.0]octan-3-one.

* * * * *